United States Patent
Bowden et al.

(10) Patent No.: US 9,302,013 B2
(45) Date of Patent: Apr. 5, 2016

(54) ACTIVE PRINCIPLE FOR MITIGATING UNDESIRED MEDICAL CONDITIONS

(75) Inventors: Tim Bowden, Uppsala (SE); Kristoffer Bergman, Stockholm (SE); Thomas Engstrand, Uppsala (SE); Lennart Soderberg, Uppsala (SE)

(73) Assignee: TERMIRA AB, Uppsala (SE)

( * ) Notice: Subject to any disclaimer, the term of this patent is extended or adjusted under 35 U.S.C. 154(b) by 50 days.

(21) Appl. No.: 13/982,492

(22) PCT Filed: Jan. 25, 2012

(86) PCT No.: PCT/SE2012/000006
§ 371 (c)(1),
(2), (4) Date: Jul. 30, 2013

(87) PCT Pub. No.: WO2012/105887
PCT Pub. Date: Aug. 9, 2012

(65) Prior Publication Data
US 2013/0302268 A1    Nov. 14, 2013

Related U.S. Application Data

(60) Provisional application No. 61/475,425, filed on Apr. 14, 2011.

(30) Foreign Application Priority Data

Jan. 31, 2011 (SE) ...................... 1100066

(51) Int. Cl.
A61K 47/48    (2006.01)
A61K 31/765   (2006.01)
A61K 31/785   (2006.01)

(52) U.S. Cl.
CPC ......... *A61K 47/48176* (2013.01); *A61K 31/765* (2013.01); *A61K 31/785* (2013.01); *A61K 47/4823* (2013.01)

(58) Field of Classification Search
None
See application file for complete search history.

(56) References Cited

U.S. PATENT DOCUMENTS

2005/0118227 A1 *  6/2005  Kohn et al. ................... 424/423

FOREIGN PATENT DOCUMENTS

WO    WO 2009 108100    *   9/2009   ............... C08L 5/08

OTHER PUBLICATIONS

Ito et al., Biomaterials, 2007, vol. 28, pp. 1778-1786.*
Ito et al., "Anti-inflammatory function of an in situ cross-linkable conjugate hydrogel of hyaluronic acid and dexamethasone", Biomaterials, 2007, vol. 28, pp. 1778-1786.
Negre-Salvayre et al., "Advanced Lipid Peroxidation End Products in Oxidative Damage to Proteins. Potential Role in Diseases and Therapeutic Prospects for the Inhibitors", British Journal of Pharmacology, 2008, vol. 153, pp. 6-20.
Guiotto et al., "Synthesis and Evaluation of Neuroprotective, β-Unsaturated Aldehyde Scavenger Histidyl-Containing Analogues of Carnosine", Journal of Medicinal Chemistry, 2005, vol. 48, pp. 6156-6161.
Guiotto et al., "Malondialdehyde scavenging and aldose-derived Schiff bases' transglycation properties of synthetic histidyl-hydrazide carnosine analogs", Bioorganic & Medicinal Chemistry, 2007, vol. 15, pp. 6158-6163.
Hamann et al., "Hydralazine inhibits compression and acrolein-mediated injuries in ex vivo spinal cord", Journal of Neurochemistry, 2008, vol. 104, pp. 708-718.
Hamann et al., "Acrolein Scavenging: a potential novel mechanism of attenuating oxidative stress following spinal cord injury", Journal of Neurochemistry, 2009, vol. 111, pp. 1348-1356.

* cited by examiner

*Primary Examiner* — Brian Gulledge
(74) *Attorney, Agent, or Firm* — Young & Thompson

(57) ABSTRACT

A composition for treating or preventing inflammatory-related conditions includes as an active principle a carrier which exhibits a plurality of a scavenger structure capable of mitigating the activity of a mediator of inflammatory-related conditions. The scavenger structure includes a nucleophilic center complying with the formula $X^1(-R''-)(-R')_m H_n$ where: a) $X^1$ is a single-bonded heteroatom selected amongst N, O and S and exhibits a free electron pair; b) m is 0 or 1 and n is 1 or 2; c) —R''— is a bivalent organic group providing attachment to the carrier via one of its free valences and to $X^1$ at the other free valence; and d) R'— is a monovalent organic group attached to the $X^1$ via its free valence. A method for treating or preventing inflammatory-related conditions in an individual suffering from such conditions includes: providing the composition; and contacting the mediator within or separate from the individual.

8 Claims, No Drawings

ACTIVE PRINCIPLE FOR MITIGATING UNDESIRED MEDICAL CONDITIONS

TECHNICAL FIELD

The present invention relates to a method and a composition for combating mediators of the inflammatory cascade of an individual. The method is primarily intended for treating and/or preventing inflammatory-related conditions, such as inflammatory-related reactions, effects and responses, and/or attenuating oxidative stress in an individual.

BACKGROUND TECHNOLOGY

Lipid peroxidation products are early stage and major mediators in the inflammatory cascade. These products include endogenous and/or exogenous aldehydes, such as 4-hydroxy-nonenal, malondialdehyde and acrolein and act by stable modification of proteins, which subsequently alter their stability and functionality upon adduct formation. Several diseases have been shown to be associated with or caused by enhanced adduct formation with aldehydes, including neurodegenerative diseases (Alzheimer, Parkinson), atherosclerosis, osteoarthritis, cataract etc.

Aldehyde and keto groups are reactive electrophiles. They will react with nucleophiles, preferentially nucleophiles containing nitrogen having a free electron pair, to form Schiff bases or imine derivatives. Subsequent rearrangement e.g. of the Amadori type, may produce a new aldehyde or keto group susceptible to reaction with yet another nucleophile. This forms the basis of protein cross-linking and subsequent denaturation.

Another in vivo aldehyde modification is the reaction of amino groups, e.g. in proteins, with carbohydrates having a reducing end with a masked aldehyde functionality. This non-enzymatic glycation produces "Advanced Glycation End products" also called AGE modifications of proteins that potentially may lead to inflammation. These reactions are related to the Maillard reaction.

Several molecules, including carnosine hydralazine etc, exhibit aldehyde scavenging properties in vitro, by trapping the aldehyde as an imine or Schiff base, but the effects are questionable or sparse when applied in vivo and in a clinical setting. The foremost reason for a limited aldehyde scavenger effect is the small sizes of these molecules which give them an unfavourable pharmacokinetic profile.

It is believed that the active principle of the inventive composition is capable of mitigating the effects an early stage mediator might have on an inflammatory-related response due to its content of reactive groups which are capable of forming covalent binding with an electrophilic carbonyl group and/or an electrophilic carbon-carbon multiple bond. The carbonyl group is in particular believed to be an aldehyde group which possibly is conjugated with a carbon-carbon multiple bond (α,β-unsaturation). Our results suggest that the favourable effect found requires the factual formation of covalent binding between our active principle and an early stage mediator via the reactive groups indicated. However, since this hasn't yet been finally confirmed, the invention is for the time being (at the filing of this specification) not linked to such a mechanism. There may still be other explanations for the favourable and surprising effects we have accomplished with our active principle containing selected carrier-bound reactive nucleophilic groups.

The invention is concerned with two main kinds of mediators giving raise to inflammatory-related responses:

a) Endogenous mediators are formed in the individual where they exert their effects. This group includes as one subgroup mediators/substances which are part of a response leading to inflammation and as a second subgroup mediators/substances which are capable of causing undesired effects which can be considered as part of an inflammatory-related response but not necessarily as inflammation, e.g. discomfort, head-ache, hangover, cataract etc., and b) Exogenous mediators are formed outside the individual where they exert their effects.

They are capable of causing an inflammatory-related effect in vivo, and/or have to be transformed in vivo to an endogenous mediator before such an effect can be accomplished.

Inflammatory-related conditions (as well as inflammatory-related reactions and effects) will in the context of the invention encompass inflammation as well as the undesired conditions discussed in the preceding paragraphs if not otherwise indicated.

Illustrative scientific articles and patent documents concerning aldehyde containing mediators and/or scavenging of such mediators are:

1. Burcham et al., WO 2003055487 Method of controlling damages mediated by α,β-unsaturated aldehydes.
2. Burcham et al., WO 2006002473 Method of controlling damages mediated by α,β-unsaturated aldehydes.
3. Cho et al., WO 2009091992 Repairing damaged nervous system tissue with nanoparticles.
4. Guitto et al., Synthesis and evaluation of neuroprotective α,β-unsaturated aldehyde scavenger histidyl-containing analogues of carnosine. J. Med. Chem. 48 (2005) 6156-6161.
5. Guitto et al., Malondialdehyde scavenging and aldose-derived Schiffs bases' transglycosylation properties of synthetic histidyl-hydrazide carnosine analogs. Bioorg. Med. Chem. 15 (2007) 6158-6163.
6. Hamann et al., Hydralazine inhibits compression and acrolein-mediated injuries in ex vivo spinal cord. J. Neurolog 104 (2008) 708-718
7. Hamann et al., Acrolein scavenging: a potential novel mechanism of attenuating oxidative stress following spinal cord injury. J. Neurochem 111 (2009) 1348-1356.
8. Ito et al., Anti-inflammatory function of an in situ cross-linkable conjugate hydrogel of hyaluronic acid and dexamethasone. Biomaterials 28 (2007) 178-1786.
9. Monnier et al., Wake up and smell the Maillard reaction. Sci. Aging Knowl. Environ. 50 (2002) pe21
10. Negre-Salvayre et al., "Review: Advanced lipid peroxidation end products in oxidative damage to proteins. Potential role in diseases and therapeutic prospects for the inhibitors. Br. J. Pharmacol. 153 (2008) 6-20
11. Reddy et al., Carnosine: a versatile antioxidant and anti-glycating agent. Sci. Aging Knowl. Environ. 18 (2005) pe12

The synthesis and use of polymers exhibiting covalently attached aldehyde-reactive functionalities or aldehyde groups have been described in WO 2009108100 (IPR-Systems AB) and references cited therein. The publication indicates that the hydrogel formed by reaction of these two differently functionalized polymers with each other in vivo may be highly biocompatible causing low or no host defence reaction including low or no inflammation. Nothing has been concluded about the reason for this.

OBJECTS

The primary goal with the present invention is to at least partially improve the effect of earlier suggested low molecular weight substances for inhibiting mediators of the above-mentioned type, i.e. to improve the treatment and/or prevention of inflammatory-related effects of the mediators. The improvements may be related to a) the therapeutic effect when treating and/or preventing inflammation and/or other inflammatory-related conditions,
b) the versatility of the use of agents mitigating undesired effects of endogenous and/or exogenous inflammatory-related mediators,
c) the pharmacokinetics of the active principle in order to accomplish a higher and/or prolonged effect, etc.

INVENTION

The present inventors have recognized that immobilization of relevant scavenger functionalities to a macromolecular carrier would improve the effects of the corresponding low molecular weight scavenger molecule. Unexpectedly it has been found that the optimal functionalities have been found amongst reactive groups that normally are used for cross-linking macromolecular carriers and/or for the synthesis of carrier-bound therapeutic active entities (WO 2009108100 and references cited therein).

In the present specification our principle is demonstrated by the synthesis of functionalized carriers which are capable of aldehyde scavenging. In the experimental part this kind of construct is shown to inhibit oxidation of human albumin by acrolein in a dose-dependent manner in vitro (example 1). Further, the in vivo effect on inflammation is demonstrated both in rodents and humans using a wound healing model (example 2 and 3). The effect on lowering inflammatory-related mediators in tobacco smoke is also demonstrated (example 4).

First Main Aspect (Composition)

The first aspect is a composition for treating or preventing inflammatory-related conditions in an individual suffering from or being at risk for suffering from such conditions. The main characteristic feature is that the composition comprises as an active principle (=AP) a carrier which exhibits a plurality of a scavenger structure which when present on the carrier is capable of mitigating and/or neutralising the activity of a mediator of inflammatory-related conditions.

Second Main Aspect (Method)

The second main aspect of the invention a method for treating or preventing inflammatory-related conditions in an individual suffering from or being at risk for such conditions. The main characteristic feature of the method comprises the steps of:

i) providing a composition containing as an active principle (=AP) a carrier which exhibits a plurality of a scavenger structure which is capable of mitigating and/or neutralising the activity of a mediator of inflammatory-related conditions, and
ii) contacting AP with said mediator a) within said individual, or b) separate from said individual.

Alternative (a) means that the composition containing AP is administered to said individual.

The individual is typical an animal, such as a vertebrate, with particular emphasis of a mammal such as a human being. In the case the method is a therapeutic treatment the individual is typically a patient.

The mediator may be water-soluble or water-insoluble. The mediator is typically of the same kind as mediators participating in an early stage of inflammatory-related conditions (=early stage mediator) and is as such typically of a low molecular weight, such as ≤3000 dalton or ≤2000 dalton or ≤1000 dalton or ≤500 dalton. This does not exclude that there are mediators of molecular weights ≥3000, e.g. exhibiting biopolymeric structure, such as protein/polypeptide structure and/or carbohydrate structure and/or nucleic acid structure.

Step (ii) means that the inflammatory-related effects caused by a mediator is mitigated by neutralization of the mediator.

Step (ii.a) means that the contacting and neutralization of the mediator is taken place in vivo, i.e. within the body, on the skin etc of the individual suffering from or being at risk for inflammatory-related conditions involving the mediator Step (ii.b) encompasses two main situations:

A) The mediator is present in a fluid, tissue, organ etc, which originates from an individual. The fluid, tissue, organ etc is after neutralization of the mediator delivered to an individual suffering from or being at risk for inflammatory-related conditions, i.e. the contacting and the neutralization of the effect of the mediator are taking place ex vivo and/or extracorporeal. The mediator is primarily endogenous but may also be exogenous. The individual receiving the treated fluid, tissue, organ etc may be the individual from which the fluid, tissue, organ etc originates, or some other individual.
B) The mediator is present in a fluid, which does not originate from an individual, e.g. ambient atmosphere, gas to be inhaled, water etc and typically has a non-biological origin. The fluid is after the neutralization of the mediator allowed to be in contact with the individual suffering from or being at risk for inflammatory-related conditions, i.e. the contacting and the neutralisation of the effect of the mediator are taking place in vitro and external to the individual suffering from or being at risk for inflammatory-related conditions. The mediator is typically exogenous and the neutralization is taking place before the mediator is brought into contact with the individual suffering from or being at risk for inflammatory-related conditions. Typical routes for bringing the fluid in contact with the individual after neutralization of the mediator are inhaling, oral, dermal etc.

The Composition

The composition may contain one or more formulations where at least one of them comprises AP or reagents necessary for the formation in vivo of AP (e.g. as described in WO 2009108100 for compositions used for formation in vivo of extracellular matrices).

The Active Principle (=AP)

AP comprises a carrier exhibiting the plurality of the scavenger structure. Every scavenger structure is firmly attached to the carrier, for instance covalently. AP as well as the carrier as such may be soluble or insoluble in aqueous liquids such as water, body fluids, such as blood, serum, plasma, urine, lymph, lachrymal fluid, intestinal juice, gastric juice, saliva, synovial fluid etc.

AP may be fixed to a water-insoluble support that may be of various physical and/or geometric appearances depending on the intended use. See further below.

Either one or both of the carrier and the support should be inert in the sense that they should not participate as competing reactants in the reaction between the scavenger structure and the mediator. Both of them should have an acceptable biocompatibility causing low or no host defence reactions including low or no inflammation.

The Scavenger Structure

The scavenger structure when present on the carrier mitigates and/or neutralizes the activity of the mediator. The mitigation/neutralization may be irreversible or reversible with preference for the former. It can take place by capturing the mediator to the carrier or by leaving the mediator in (=transforming the mediator to) an inactivated form which is unbound to the carrier. When capturing is at hand, the scavenger structures and reactive groups on the mediator typically react with each other leading to the formation of covalent bonding which attaches the mediator in a transformed and neutralised form to the carrier (=adduct formation).

The scavenger structure comprises a first nucleophilic centre which preferably is capable of participating in an addition reaction with the carbonyl group (C=O) of an aldehyde group,—and/or with a C,C-multiple bond to which one or more electron-withdrawing substituents preferably are directly attached. Reactive species of this kind occurring in vivo and suggested to be involved in undesired inflammatory-related effects are for instance malondialdehyde, sugar aldehydes, α,β-unsaturated aldehydes —CH=CH—CH=O, such as acrolein, 4-hydroxy-non-2-enal etc (examples of early stage inflammatory-related mediators).

The nucleophilic centre (first centre) of the scavenger structure preferably comprises a single-bonded first heteroatom N, O or S (=$X^1$) which exhibits
a) a free electron pair,
b) one or two hydrogens, and
c) one or two organic groups R'— (monovalent) and —R"— (divalent) directly bound to the heteroatom.

The preferred heteroatoms are N and S. S is preferably combined with the presence of a second nucleophilic centre, such as a primary or secondary amino, in the same scavenger structure as discussed below. The bivalent organic group —R"— provides binding to the carrier via one of its free valencies. The other free valency of —R"— as well as the free valency of the other organic group R'— are directly attached to the heteroatom $X^1$.

Generically a nucleophilic centre has the formula:

$X^1(-R''-)(-R')_m H_n$ (formula I)

where $X^1$, R'— and —R"— are as defined in the preceding paragraph and m is 0 or 1 and n is 1 or 2 with the sum of m plus n being 2 for $X^1$=N and 1 for $X^1$=S and O.

A single-bonded atom means that the atom is directly bound to other atoms only by single bonds. A multiple-bonded atom means that the atom is directly bound to another atom by a triple or a double bond. The atoms referred to are primarily N, O, S and carbon.

The preferred nucleophilic centres are typically uncharged when interacting with the mediator. For a nucleophilic centre which is an uncharged base or acid form of an acid-base pair ≥5%, such as ≥25% or ≥50 or ≥75%, of the total concentration of the acid-base pair should be in uncharged form.

When the heteroatom $X^1$ is N, the ability to react with an aldehyde group will include that the adduct formed is capable of undergoing spontaneous elimination of water ($H_2O$) to the formation of an imine structure (—CH=NR"—, m=0 and n=2) and/or an enamine structure (—CH=CHNHR"—, m=0 and n=2) or —CH=CHNR'R"—, m=1 and n=1) with both alternatives requiring a hydrogen (α-hydrogen) on a $sp^3$-hydridised α-carbon of the aldehyde group —CHO). When the heteroatom $X^1$ is S or O, m=0 and n=1 which means that the structure obtained upon elimination of $H_2O$ is thioenolate or enolate (—CH=CH$X^1$R') (provided there is an α-hydrogen of the aldehyde group —CHO). These elimination reactions typically mean formation of a more stable product and/or a product that may react further to a further stabilized "end"-product. The selection of scavenger structures containing groups permitting subsequent reactions which end up in stabilized end products will support irreversibility of the initial addition reaction, and are as a rule preferred.

The reaction of the first nucleophilic centre and a reactive C,C-multiple bond on a mediator will result in a primary adduct which comprises the structure >CH—CH$X^1$— (for C,C-double bonds) and if the multiple bond is α,β to an aldehyde group there can be formed different tautomeric adducts. e.g. —CH$X^1$—CH=CHOH (enol) and —CH$X^1$—CH$_2$—CH↑O (keto) which will enable another nucleophilic centre of the same or another scavenger structure to react with the mediator molecule ending up in stabilized end products.

Either one or both of the organic groups R'— and —R"— comprise a structure of the formula

 (formula II)

where
a) each of m', n' and o' is 0 or 1, with preference for m' being 1 with further preference for either one or both of n' and o' also being 1,
b) each of $X^2$, $X^3$, and $X^4$, is selected amongst NH and a heteroatom S or O, with preference for either one or both of $X^2$ and $X^4$ being selected amongst NH and O with further preference for $X^3$ being selected amongst NH, O and S,
c) the left free valence provides binding to a monovalent alkyl group R*— or to the carrier via at least a bivalent alkylene group —R**—, each of which comprises the methylene group —CH$_2$— shown of formula II,
d) the right free valency binds directly to the first heteroatom $X^1$.

The substructure C=$X^3$ (=B) includes also other ester- and amide-forming substructures which derive from acid functions and form an ester function when $X^2$ and/or $X^4$ are oxygen and/or an amide function when $X^2$ and/or $X^4$ are NH, e.g. sulphonamide (B is S(=O)$_2$) or phosphone amide (B is P=O(NH$_2$) or P=O(OH), n'=1).

Either one or both of the monovalent alkyl group R*— and the bivalent alkylene —R**— may be straight, branched or cyclic and possibly contain one or more structures selected amongst ethers (—O—, —S—), hydroxy (—OH), mercapto (—SH) and amino (—NH—, —NH$_2$). Each free valences represent binding to $sp^3$-hybridised carbon (=alkyl carbon). Either one or both of these alkyl groups are preferably a lower alkyl which in this context means that they comprise one, two, three, four, five up to ten $sp^3$-hybridised carbons typically with at most one heteroatom O, N and S bound to one and the same carbon. The groups are typically inert in the sense that they are not participating in the reaction which neutralises the mediator. The hydrogens given in formula (I) and/or its substructures may be replaced with an alkyl group selected amongst the same alkyl groups as discussed for R*—.

It is preferred that the bivalent group —R"— which attaches the first nucleophilic centre to the carrier comprises a substructure complying with formula I and/or II.

The structural elements (substructures) discussed in the preceding paragraphs will support delocalisation of electrons and therefore further support irreversibility of the initial addition reaction.

Preferred scavenger structures thus have a nucleophilic centre which contain the first heteroatom $X^1$ together with a structure complying with formula II and are selected amongst:
 a) amino groups preferably primary or secondary amino groups
 b) hydrazide groups such as —NH—$NH_2$, e.g. as part of a —$CONHNH_2$ group, a semicarbazide group such as —$NHCONHNH_2$, a carbazate group such as —$OCONHNH_2$, a thiosemicarbazide group such as —$NHCSNHNH_2$, a thiocarbazate group such as —OCS$NHNH_2$ (formation of hydrazone, semicarbazone, thiocarbazone linkages/groups etc when undergoing addition/elimination reactions with an aldehyde group)
 c) aminooxy groups, such as —$ONH_2$ etc (formation oxime linkages/groups etc when undergoing addition/elimination reactions with an aldehyde group),
 d) a thiol group e.g. —SH (Michael addition products are formed when the thiol group reacts with a C,C-double bond. The product may undergo keto-enol tautomerisation when the double bond is α,β to a keto- or aldehyde-carbonyl, see above).

The free valence indicated in each of the groups given in the preceding paragraph preferably attaches the nucleophilic centre to the carrier via a linker structure comprising the above-mentioned bivalent alkylene group —R**—. A hydrogen bound directly to nitrogen may be replaced with a monovalent alkyl group selected amongst the same alkyl groups as R*— as long as they are not substantially counteracting the desired reactivity of the unsubstituted form of the nucleophilic centre. Thus the hydrogen in a thiol group and in a hydroxyl group can not be replaced, for instance. Two replacing alkyl groups may form a cyclic structure together with atom to which they are attached, i.e. form a bivalent alkylene group e.g. selected amongst the alternatives for the —R**— group.

The bivalent structures —R**— and —R"— discussed above comprises next to the carrier a linker structure which does not negatively affect the desired effect of the nucleophilic centre of the scavenger structure. Such structures are not part of the invention and suitable such structures can be designed by the average-skilled person in the field.

In certain preferred scavenger structures there may be a second nucleophilic centre which a) may be part of one of the organic groups, e.g. the R*— or the —R**— group, and b) contain a first heteroatom N, O or S ($=Y^1$) in the same manner as for the first nucleophilic centre. In principle this means that this second nucleophilic centre complies with the formula:

$Y^1(-R''-)(-R')_m H_n$ (formula III)

and the formula

—$CH_2(Y^4)_{o''}(C=Y^3)_{n''}(Y^2)_{m''}$ (formula IV)

where m, n, m", n", o", $Y^1$, $Y^2$, $Y^3$, $Y^4$, —R"— and —R' are selected in the same groups of variables as m, n, m', n', o', $X^1$, $X^2$, $X^3$, $X^4$, —R"— and —R' of formula I and II. This includes that hydrogens (H) may be replaced as suggested for formulae I and II.

The heteroatom $Y^1$ preferably is part of
 a) an —$NH_2$ group where the free valence preferably may bind to a $sp^3$-hybridised carbon, or
 b) a thiol group —SH where the free valence preferably may bind to a $sp^3$-hybridised carbon.

Each of m", n" and o" in formula IV is 0 in both (a) and (b).

The distance between the first heteroatom $Y^1$ and the first heteroatom $X^1$ is typically larger than two or three atoms with upper limits being e.g. 20 atoms with preference for 4, 5 or 6 atoms between these two heteroatoms. The distance should support intra-molecular cyclisation, typically via one or more addition reactions. This cyclisation typically comprises an addition reaction between the second nucleophilic centre and
 a) a carbon-carbon or a carbon-heteroatom double bond formed as described above by reaction of the first nucleophilic centre with the starting aldehyde group, and/or
 b) a reactive multiple C,C-bond present already in the starting aldehyde, such as a reactive double C,C-bond, e.g. α,β to the aldehyde group, and/or
 c) a second keto or aldehyde carbonyl group provided such a group is present in the mediator molecule.

The result of the cyclisation is an n-membered ring-structure containing the first heteroatom $Y^1$ and the first heteroatom $X^1$ with n in n-membered being an integer ≥3 with preference for 5 or 6. Larger rings may also be formed, such as 7-, 8-, 9-, 10-, 11-, 12-, 13-, 14-membered rings, as long as steric considerations and relative positions of functional groups so admit. The cyclisation may be followed by rearrangement reactions, e.g. intramolecularly, and/or elimination reactions creating carbon-heteroatom double bond(s), ring-openings etc.

The Carrier

The selection of suitable carriers depends on the requirements of a particular use. The typical carrier is selected amongst macromolecular compounds, i.e. is a compound which has a molecular weight of ≥2000 dalton, preferably ≥10000 dalton or ≥50000 dalton, and preferably exhibits a polymeric structure, i.e. is a polymer which may be a homopolymer, copolymer or a chemical adduct between two or more polymers of different polymeric structure. Other suitable carriers may have molecular weights ≤2000 dalton and exhibit polymeric structure as indicated by the possibility of the low numbers of monomeric units discussed below, e.g. ≥20 and ≤100. The term "adduct polymer" in this context means a product formed by reacting two polymers exhibiting mutually reactive groups capable of forming covalent bonds that link the two polymers together upon reaction of the two mutually reactive groups with each other. See for instance WO 2009108100 (IPR-Systems AB) and references cited therein. Suitable macromolecular carriers may thus be selected amongst synthetic polymers (=man-made polymers), biopolymers (nature-made polymers such as polysaccharides, polypeptides, proteins etc) and biosynthetic polymers where "biosynthetic polymer" refers to a macromolecular carrier or compound exhibiting both a synthetic polymeric structure and a biopolymeric structure. A carrier polymer may be cross-linked or not cross-linked. With respect to branching the polymer may be unbranched, i.e. linear, or branched including either hyperbranched or dendritic. The degree of branching may thus vary between 0 and 1, such as be ≥0.10 or ≥0.25≥0.5≥0.75 or ≥0.90 and/or ≤0.90 or ≤0.75 or ≤0.50 or ≤0.25 or ≤0.10. Cross-linked polymers are as a rule insoluble in aqueous liquids while the solubility of non-cross-linked polymers depend on the overall structure of the polymer, e.g. presence and amount of polar and/or hydrophilic groups.

Carrier polymers may also be derivatized to contain non-polymeric or polymeric groups, for instance cross-links, substituents, charged or uncharged groups, scavenger structures (as discussed above) etc. Macromolecular carriers which are insoluble in aqueous liquids may have different physical and geometric shapes as discussed for support materials elsewhere in this specification.

The term polymer above includes organic as well as inorganic polymers.

The macromolecule or polymer used in the carrier may be water-insoluble and suspensible in aqueous liquid media (when in particle form).

Polymers and other macromolecules suitable as carrier material may be hydrophilic or hydrophobic with preference for hydrophilic. Pronounced hydrophobic macromolecular carriers are as a rule insoluble in aqueous liquids meaning that there may be a risk for host defence reactions with them and also that the availability of nucleophilic centres for reaction with inflammatory-related mediators may not be optimal. In order to overcome this kind of problems, it is often preferred to introduce hydrophilic groups on their surfaces (hydrophilization). The introduction of hydrophilic groups may among others be accomplished by a) coating with a hydrophilic material,
b) selecting building blocks/monomers which exhibit hydrophilic groups and appropriate conditions during synthesis of the macromolecular compound, and
c) chemical derivatisation with hydrophilic groups subsequent to the synthesis of the basic hydrophobic polymer etc.

The hydrophilicity of a group, structure or carrier molecule increases as a rule with an increase in the ratio r=the sum of the number of heteroatoms O, N and S divided by the sum of the number of carbon atoms. Hydrophilic groups/compounds typically have an $r \geq 0.5$, preferably $\geq 1.0$, and for hydrophobic groups $r<1.0$, preferably $\leq 0.5$. Typical hydrophilic groups are hydroxy, amino, amido, carboxy (including free acid carboxyl as well as carboxylate (ester ester and salt) etc. Typical hydrophobic groups are alkyls ($C_nH_{(2n+1)}$—, $C_nH_{(2n-1)}$—, $C_nH_{(2n-3)}$— etc), phenyls including alkyl phenyls, benzyl including other phenylalkyls etc. A carrier macromolecule typically comprises a polymer backbone which comprises $\geq 5$, or more preferably $\geq 10$ such as $\geq 25$ different and/or identical monomeric units linked together. The polymer may carry projecting or pending polymeric and/or non-polymeric groups of various lengths and kinds. A carrier polymer is preferably hydrophilic with hydrophilic groups selected amongst those given elsewhere in this specification. The most preferred hydrophilic group is hydroxy with the preferred carrier polymers and/or other macromolecular carrier being selected by poly hydroxy polymers (PHP or PH-polymers) exhibiting $\geq 5$, with preference for $\geq 10$, such as $\geq 25$ or $\geq 50$ hydroxyl groups and/or $\geq 5$ monomeric subunits each of which exhibits one, two, three, four or more hydroxyl groups per unit.

Typical polymers that may be present in polymeric carriers are a) polyester polymers, b) polyamide polymers, c) polyether polymers, d) polyvinyl polymers, e) polysaccharides etc. A carrier may comprise one or more of these polymers/polymeric structures.

Polyester polymers are in particular obtained by polymerisation of a) monomers exhibiting at least one hydroxy group and at least one carboxy group, or b) a mixture containing monomers exhibiting two or more hydroxy groups and monomers exhibiting two or more carboxy group.

Polyamide polymers are in particular obtained by polymerisation of a) monomers exhibiting at least one amino group and at least one carboxy group, or b) a mixture containing monomers exhibiting two or more amino groups and monomers exhibiting two or more carboxy group.

An important group of polyamides are those that exhibit polypeptide structure together with a plurality of hydroxy groups (PH-polymers). Suitable polyamide polymers of this kind are typically based on hydroxy-,amino-carboxylic acids as monomers, in particular with the amino group positioned a to the carboxylic group, e.g. serine, threonine, tyrosine, proline etc.

Polyether polymers are typically used in combination with other polymeric structures, e.g. polymers of (a), (b), (d) and/or (e) above, which are polyfunctional with respect to the presence of groups such as hydroxy, amino etc. Typical polyether polymers are polyethylene oxide and various copolymerisates between ethylene oxide and other lower alkylene oxides, lower epihalohydrins etc.

Polyvinyl polymers which may be suitable as polymeric carriers in the invention are typically found amongst polymers containing one, two or more different monomeric units selected amongst hydroxyalkyl acrylates and methacrylates, N-hydroxyalkyl acryl- and N-hydroxyalkyl methacrylamides, hydroxyalkyl vinyl ethers, vinyl esters etc. Polyvinyl alcohols are typically obtained by partial hydrolysis of polyvinyl esters meaning that polyvinyl alcohols that are preferred in the invention typically exhibit residual amounts of ester groups ($\leq 10\%$ or $\leq 5\%$).

Typical polysaccharides that may be present in carriers used in the invention include dextran, starch, agarose, agaropektin, cellulose, glucosamino glucanes (GAG), and derivates of these polysaccharides etc. The most interesting polysaccharides are dextran, certain glucosamino glucanes (GAG) such as hyaluronic acid etc.

A polymer to be used in the carrier may have been derivatized, e.g. cross-linked and/or functionalized after its synthesis.

The scavenger structure including the first, the optional second nucleophilic centre and the various heteroatoms discussed for the scavenger structures are typically part of one and the same organic group/substituent attached to the macromolecular carrier. In certain variants different parts of a scavenger structure may be part of different groups/substituents attached to the carrier and/or part of the carrier.

Sizes/molecular weights of suitable carrier polymers will among others depend on the actual application/use of the composition/method of the invention. Thus suitable polymeric carriers with respect to a particular polymeric structure and/or size may vary within a wide interval. Thus as a rule the number of monomeric subunits (mean value) of a polymer present in the carrier may be $\geq 20$ or $\geq 100$ or $\geq 200$ or $\geq 300$ or $\geq 500$ or $\geq 1000$ or $\geq 2000$ or $\geq 20\,000$ or $\geq 50\,000$ and/or $\leq 50\,000$ or $\leq 20\,000$ or $\leq 2000$ or $\leq 1000$ or $\leq 500$ or $\leq 300$ or $\leq 200$, or $\leq 100$ (with the proviso that $\geq$-limit always is lower than a $\leq$-limit when these values are combined to define intervals). Preferred numbers of monomeric units may in some cases be found in the interval of 200-600 which in particular applies to the polyvinylalcohol used in the experimental part.

Suitable numbers of scavenger structures or nucleophilic centres per monomeric unit of a polymer of the carrier will also depend on the use, the scavenger structure, the mediator etc and may thus be found within a wide interval, such as $\leq 80\%$, such as $\leq 50\%$ or $\leq 20\%$ with typical lower limits being 0.01% or 0.1% or 1% where 100% corresponds to one scavenger structure or nucleophilic centre per monomeric unit. For scavenger structures containing two or more nucleophilic centres the number of nucleophilic centres per monomeric unit may exceed 100%, such as $\geq 100\%$ or $\geq 125\%$ or $\geq 150\%$.

Other Features of the Composition

AP is present in the composition as an AP-formulation in which AP is:

a) in dry form, for instance as free particles,
b) in dissolved form, typically in an aqueous liquid medium, and c) in suspended/dispersed form, i.e. as water-insoluble particles suspended in an aqueous liquid medium,
d) attached to a support which is insoluble in aqueous liquid media.

The term "dissolved" in this context means that AP is present as a solute. AP particles comprise AP in a pure form or diluted with some solid material. Useful concentrations of AP in formulations according to (b) can be found within a broad interval. For liquid formulations e.g. within the interval of 0.1 µg-100 mg/mL.

The composition may in addition to AP contain buffers, salts etc required for enabling acceptable conditions in vivo for the patient and for the reaction of AP with an inflammatory-related mediator to occur. These constituents may be co-formulated with AP in the AP-formulation.

A potentially important variant of the inventive composition comprises formulations enabling production of cross-linked carrier polymers exhibiting a plurality of a nucleophilic structure that can be used as a scavenger structure (WO 2009108100, IPR-systems AB and references cited therein). The cross-linking may take place in vivo or ex vivo. In this variant the AP-formulation of the inventive composition is represented by at least two subformulations:

1) a first subformulation containing a macromolecular carrier exhibiting a plurality of a reactive nucleophilic group which has the potential of acting as a scavenger structure for an inflammatory-related mediator of the kinds discussed above, and
2) a second subformulation containing a cross-linking reagent, preferably in the form of a polymer, and exhibiting (comprising) a plurality of a reactive electrophilic group which is capable of reacting in aqueous media with the reactive nucleophilic group of the macromolecular carrier to the introduction of covalent cross-links in the macromolecular carrier.

The macromolecular carrier in the first subformulation may be selected amongst the macromolecular carriers discussed above. When the cross-linking reagent in the second subformulaion is a polymer this polymer may be selected amongst the polymeric macromolecular carriers discussed above.

The cross-linked carrier obtained by mixing the first subformulation with the second subformulation will contain a plurality of scavenger structures if the reactive nucleophilic group at the time of mixing is in molar excess compared to the reactive electrophilic group. Molar excess in this context typical means excess with a factor ≥2, such as ≥5 or ≥10 or ≥20. If the starting carrier and the cross-linking reagent is properly selected the obtained product will form a hydrogel in situ.

It can be envisaged that this kind of two-component compositions may be advantageous when administering by injection highly viscous solutions of high-molecular weight hyaluronic acid (desired polymer). Highly viscous solutions of hyaluronic acids are difficult to inject and administration of hyaluronic acid is often linked to a risk for adverse effects due to inflammatory-related reactions. These problems are likely to be reduced by injecting at the same location of a patient a composition comprising:

a) a first subformulation in which the macromolecular carrier is a low-molecular weight variant of hyaluronic acid in dissolved form (=a variant having a lower Mw than the Mw of the desired hyaluronic acid), and
b) a second subformulation in which the cross-linking reagent is also a low-molecular weight variant of hyaluronic acid in dissolved form, with the proviso that i) that the reactive nucleophilic group in the first subformulation is in excess compared to reactive electrophilic groups in the second subformulation, and
ii) that the degree of substitution with respect to reactive electrophilic groups on the hyaluronic acid of the second subformulation (cross-linking reagent) is sufficiently low for producing a carrier in dissolved form, i.e. non-gel form, when the two subformulations are mixed with each other upon injection.

The mixing leads to a reaction between the reactive nucleophilic group and the reactive electrophilic group to the formation of a covalent cross-linking structure. Experimental testing is required for finding optimal degrees of substitution with respect to the reactive electrophilic group in the second subformulation relative to other reaction variables in order to obtain a carrier product in dissolved form, i.e. non-gel form.

The injection of the subformulations is preferably done in parallel, for instance with mixing of the formulations in the used syringe during or just before the injection is started. The techniques for this kind of injections and syringes to be used are well-known in the field; see for instance WO 2009108100 (IPR-Systems AB).

Synthesis of the Active Principle

AP may be synthesized according to well-known protocols, for instance of the kinds given in WO 2009108100 (IPR-Systems AB) and references cited therein.

Water-Insoluble Support

As mentioned above AP may be fixed to a water-insoluble support. This support material may be selected amongst support materials that have at least one or more of the following characteristics: a) in the form of particles, b) porous or non-porous particles or monoliths allowing or not allowing, respectively, aqueous liquids and/or inflammatory-related mediators to be neutralized to penetrate the support, c) rigid, d) soft, e) elastic, f) compressible, g) gellable (in particular to form a hydrogel when placed in contact with water) etc. The support may comprise plastics, glass, mineral, metal etc. When the carrier of AP is insoluble in aqueous media the carrier as such may define its own solid support.

Supports may be designed as devices to be used in vivo and/or separate from an individual suffering from or being at risk for the inflammatory-related conditions to be treated or prevented. Typical devices are implants having AP exposed on their surface, e.g. stents, vascular prosthesis, nets, teeth, bones, joints etc, patches, surgical dressings, plasters, filters, sutures, contrast media in the form of particles etc. This also includes filter and adsorbent material for a) removing the activity of inflammatory-related mediators and/or other functionally similar environmental irritants from non-biological fluids that are or will be brought in contact with animals including humans and/or b) ex vivo use, e.g. comprising removal of inflammatory-related mediators from biological fluids which derive from an individual and subsequently are to be returned to an individual suffering from or being at risk for inflammatory-related conditions. Typical examples of non-biological fluids to be treated according to (a) are air containing smoke, e.g. tobacco smoke, and industrial off-gases. Typical examples of biological fluids to be treated according (b) are blood, serum, plasma etc.

Suitable supports typically comprise polymeric materials, e.g. comprising one or more polymer selected from the same polymers as the carrier polymers are selected. Typical carrier polymers are polysaccharides, e.g. cellulose, cross-linked dextran, agarose such as cross-linked agarose etc, polyester polymers e.g. lactic acid copolymers such as polyglactin, polyethylenes etc. Other kinds of support material may also be used, e.g. ceramic materials, plastics, mineral materials, metals, composite material, activated carbon etc. Porous forms of theses materials may be used as filters and/or adsorbent material.

Attachment to the support may be accomplished by mixing, coating, impregnating etc the support with AP according to techniques known in the field. Alternatively, the macromolecular carrier of AP may be part of the material from which a support/device is made.

Contacting AP with an Inflammatory-Related Mediator (Step (ii) of the Method)

As discussed above the contacting of AP with the mediator may take place in vivo of or separate from the individual to be treated.

The amount of AP in the composition which is brought into contact with the mediator is effective in the sense that the inflammatory-related response to be treated is mitigated and/or neutralised to an acceptable level. The suitable dosage (per administration) for in-vivo applications depends on the particular medical indication, formulation (e.g. kind of, support material, AP, scavenger structure, concentrations etc) etc and thus is selected within a broad interval, e.g. $10^{-12}$-$10^2$ g with $10^{-6}$-$10^{-3}$ g as particularly interesting interval. Experimental testing is needed for individual cases.

Contacting in vivo comprises administration of the inventive composition systemically or locally depending on the particular medical indication treated and/or formulation used. Local administrations such as topical, dermal, nasal, intravitreal, intra-articular, oral, rectal, intra-osseous etc are typically used when the condition to be treated is localised to the area of administration or at a location reachable for AP from this area. Systemic administrations such as parenteral administration, e.g. intravenous and subcutaneous administration or enteral administration, e.g. oral administration etc, are mainly used when the conditions to be treated are occurring at locations not easily reachable by local administrations. Compare the discussion below on different medical indications.

Medical Indications in which it May be of Interest to Apply the Present Invention are:

1. Prevention of adherence due to evoked inflammatory reaction during surgery or caused by inflammatory diseases, e.g. intestinal adherence evoked by abdominal surgery or intestinal inflammation, tendon adherence etc. AP may be delivered locally, for example in the abdominal cavity at the time of surgery.

Formulation: Solution, dispersion, gel possibly in situ formed hydrogel etc.

Administration: Locally with a syringe or spray device.

2. Spinal cord injury. AP may be administrated systemically or locally, preferably at an early stage within hours after the trauma thus hindering oxidative stress and reduction of secondary injury processes.

Formulation: Solution, dispersion, gel possibly in situ formed hydrogel etc.

Administration: Locally at the site of injury, systemically by parenteral intravenous infusion or infusion into cerebrospinal fluid.

3. Burn injury and other large trauma. These conditions are known to dramatically enhance the systemic oxidative stress to the patients. The systemic delivery of AP may be beneficial to improve recovery and diminish secondary injury processes.

Formulation: Solution, dispersion etc.

Administration: Systemically, preferably by parenteral intravenous infusion.

4. Reperfusion injury involves inflammatory mediators including lipid peroxidation products which severely affect tissues and recovery. Reperfusion injury plays a role for example in stroke and brain trauma but also in cardiac arrest. The administration of AP may help to reduce reperfusion injury.

Formulation: Solution, dispersion etc.

Administration: Preferably by systemic parenteral intravenous or infusion into cerebrospinal fluid.

5. Aging. This process affects all living animals including humans. The balance between oxidative stress and the biological defence against oxidative stress is progressively disrupted by aging leading to accumulation of oxidized proteins and nucleic acids. Systemic delivery of AP could potentially restore this balance partially by lowering oxidative stress and slow down senescence.

Formulation: Solution, dispersion tablets etc.

Administration: Systemic, preferably by peroral administration but also parenteral.

6. Neurodegenerative diseases, e.g. Alzheimer and Parkinsons diseases. Growing evidences show a correlation between neuronal degeneration and oxidative stress including enhanced lipid peroxidation end products and the deposition of insolvable plaques in the brain. The disruption of this cascade by systemic delivery of AP may prevent the development of neourodegenerative diseases.

Formulation: Solution, dispersion tablets etc.

Administration: Preferably by systemic peroral or parenteral intravenous or infusion into the cerebrospinal fluid.

7. Oxidative stress and inflammation in blood vessels. This is known to cause endothelial dysfunction and atherosclerosis which may be prevented or treated by AP of the invention administered systemically.

Formulation: Solution, dispersion tablets etc.

Administration: Preferably by peroral or parenteral intravenous infusion.

8. Osteoarthritis-rheumatic disorders-localized cartilage defects. Lipid peroxidation products play an essential role in the development of damaged cartilage or lack of cartilage regeneration. The systemic or local delivery of AP into affected joints may help restore cartilage or stop cartilage degradation by interrupting oxidative stress to the joint.

Formulation: Solution, dispersion, hydrogel etc.

Administration: Typically local intra-articular injection or systemic peroral or parenteral administration.

9. Asthma and chronic obstructive pulmonary disease (COPD). These are common diseases characterized by inflammation in the lungs. Oxidative stress, including lipid peroxidation products, induces the production of pro-inflammatory molecules. The local administration by inhalation of AP may diminish the inflammation in the lungs.

Formulation: Solution, dispersions, particles etc

Administration: Typically by inhalation or parentral or peroral systemic.

10. Severe alcohol intake is associated with hang over. The alcohol metabolite acetaldehyde and its concentration are highest at the time of hang-over. The blocking of acetaldehyde via systemic administration of AP may therefore diminish the symptoms associated with hang over.

Formulation: Solution, dispersion, syrup, tablet, capsules etc

Administration: Systemic peroral or parenteral.

11. Pain including headache and migraine associated with environmental irritants, e.g. tobacco smoking. Lipid peroxidation products, including acrolein, from tobacco smoke or other environmental irritants may evoke pain. For example, acrolein may induce the release of calcitonine gene-related protein (CGRP) via a specific receptor TRP 1. CGRP mediates neurogenic inflammation and meningeal vasodilatation associated with headache and migraine. AP administrated locally in oral and nasal mucosa may prevent or treat the pain.

Formulation: Solution, dispersion, particles etc as nasal or oral spray, nasal drops, mouth rinse liquid etc Administration: Local delivery or systemic peroral or parenteral.

12. Cataract is characterized by age-related accumulation of oxidized proteins in the lens which may be prevented by local AP administration, e.g. eye drops.

Formulation: solutions, dispersion, particles etc.

Administration: Intravitreal or by eye drops.

13. Dry eyes are associated with local oxidative stress and the amounts of products of oxidative reactions is increased in tear fluids in affected patients. Administration of AP may be beneficial in the treatment or prevention of the disease. AP may also be beneficial for the treatment of general eye discomfort, e.g. pain and irritation due to allergic or inflammatory reaction in the conjunctiva and/or cornea and after eye surgery.

Formulation: Solutions, hydrogel

Administration: Locally as eye drops or gel.

14. Peritoneal dialysis is effective in the treatment of renal failure. After some years peritoneal dialysis often becomes less effective due to progressive ultrafiltration failure. The consequences of oxidative stress from dialysis solution may be prevented by using AP added to the dialysis solution which may diminish structural changes in the peritoneal barrier with less fibrosis.

Formulation: Solution, dispersion, dispersible particles

Administration: As part of the dialysis solution

15. Inflammatory bowel disease, such as Crohns disease and ulcerative colitis. These diseases may potentially be treated by AP, preferably by peroral or rectal administration.

Formulations: Solution, dispersions, tablets, capsules, syrups etc.

Administration: Oral, per rectal or parenteral.

16. Surgical or traumatic skin wound healing and improved scar formation. AP is delivered locally at the site of the wound or incision by injection.

Formulation: Solution, dispersion, gel possibly in situ formed hydrogel etc.

Administration: Typically local subcutaneous or intracutaneous injection.

Typical Devices to which the Present Invention can Apply.

1. Implants. Local or systemic inflammatory reaction may be caused by implants in animals or humans. Incorporation of AP within the implant or covering the surface of implants with AP could improve biocompatibility and prevent rejection or other associated complications.

2. AP immobilized on filters used for extracorpeal procedures, e.g. hemodialysis and plasmapheresis, may trap circulating lipid peroxidation products thus diminish oxidative stress to the patient.

3. Surgical or traumatic skin wound healing and improved scar formation. AP may be incorporated into surgical device used such as an impregnated suture or surgical dressing.

4. Chronic and diabetic skin wounds. These wounds are caused by reduced blood supply to the skin area. Hypoxia is associated with enhanced oxidative stress and the presence of lipid peroxidation end products. AP administrated locally by the use of a functionalized device, e.g. dressing, plaster or particles may reduce oxidative stress and improve healing and reduce healing time of the wound.

5. Fluids containing environmental irritants. The exposure to acrolein from cigarette smoke or other environmental pollutants may cause severe lung injury and negative systemic effects in humans. Acrolein could effectively be trapped by cigarette filters or breathing filters designed with AP, e.g. functionalized cellulose filter.

EXPERIMENTAL PART

Synthesis of Carbazate-Functionalized Polyvinyl Alcohol (PVAC)

Polyvinyl alcohol (5 g, 13-23 kDa) was dissolved in dimethyl sulfoxide (100 mL) while stirring for 1 hour at 80° C. under argon gas. Carbonyl diimidazole (10 g) was added and stirring continued at room temperature over night. Hydrazine hydrate (10 mL) was then added, the reaction stirred over night, and the product collected and purified by repeated precipitation in ethanol. The degree of substitution was determined spectrophotometrically by performing a trinitrobenzene sulfonic acid assay described elsewhere (Stephen L. Snyder and Philip Z. Sobocinski; Analytical Biochemistry 64, 284-288, 1975).

Example 1

The Effect of PVAC on Acrolein-Induced Protein Oxidation was Shown In Vitro

Eighty micrograms of human albumin was treated with 25 µL of 0.2 µM acrolein for 8 hs at 22° C. Protein oxidation involves the introduction of carbonyl groups into protein side chains. These carbonyl groups will react with 2,4-dinitrophenylhydrazine (DNPH) to give 2,4-dinitrophenylhydrazone (DNP-hydrazone) (Oxyblot Protein Oxidation Detection Kit, Millipore). The oxidized proteins were separated on 12% polyacrylamide gels, transferred to polyvinylidine diflouride membrane (Hybond-P, GE Health Care) and Western blot was performed using anti-DNP antibodies followed by HRP-labelled secondary antibody and visualized by using the ECL method. Solutions of PVAC (12.7% degree of substitution) having carbazate concentrations of 1 mM and 10 mM were prepared and mixed with albumin prior adding acrolein to the samples. The blots show diminished protein oxidations in PVAC treated samples as compared to controls and the effect is dose-dependent.

Example 2

The Anti-Inflammatory Effect of PVAC Demonstrated in a Rat Wound-Healing Model

An inflammatory skin reaction was evoked by surgical full-thickness skin incision and subsequent closure with resorbable polyglactin (4.0 Vicryl, Ethicon). In the experimental group the suture was treated with PVAC (10% degree of substitution of carbazate groups) by incubation in 16.5 mg/mL of PVAC in PBS (32 mM carbazate concentration) for 1 hour at room temperature and the sutures were air-dried over night. In the control group sutures were either treated in the same manner using 16.5 mg/mL of non-modified PVA or left untreated. Inflammatory reactions were grossly examined five days after surgery where the wounds closed with PVAC-impregnated sutures had almost no redness or swelling as compared to controls. The histological picture also demonstrated less inflammatory cells without giant cells present in the PVAC group at this time-point, which validates the anti-inflammatory effects of PVAC. The inhibition of inflammation during wound healing also seems to affect late scar formation, which was shown after 8 weeks in one animal with almost invisible scar at the PVAC-treated site.

Example 3

The clinical validation of the anti-inflammatory effects of PVAC was shown in a human skin wound-healing model. The experiment was performed as described in example 2 with the following exceptions: The experimental full-thickness skin incision towards subcutaneous fat was 4 cm in length and closed by PVAC treated vicryl 4.0 sutured intracutaneously instead of transcutaneous single sutures. The control incision was closed by untreated suture. Gross inspection after 1 week demonstrated almost no signs of inflammation including swelling and redness at PVAC treated site, whereas in the control the surgical incision and suture evoked an apparent inflammatory reaction.

Example 4

The effect of PVAC on acrolein-mediated protein modification from cigarette smoke was demonstrated. PVAC at concentration of 4 mg/mL (10 mM) and volume 200 µL was dispersed within filters in filter cigarettes (Marlboro) and allowed to air-dry at room temperature for 4 h. Smoke from PVAC-treated cigarettes or non-trated controls was subsequently air-bubbled into solution of human serum albumin in PBS (4 ug/ml, Sigma-Aldrich). Smoke-treated albumin solutions were subsequently analysed by western blot using mouse anti-acrolein antibody (Abcam, Cambridge, U.K) and HRP-labelled anti-mouse secondary antibody (R&D Systems, Minneapolis, Minn., U.S.A.). The signals were visualized using the ECL method. The results show a reduction of acrolein-modified albumin by 30-50% in PVAC-treated group as compared to non-treated control.

While the invention has been described and pointed out with reference to operative embodiments thereof, it will be understood by those skilled in the art that various changes, modifications, substitutions and omissions can be made without departing from the spirit of the invention. It is intended therefore that the invention embraces those equivalents within the scope of the claims which follow.

The invention claimed is:

1. A composition for treating or preventing inflammatory-related conditions comprising an active principle (=AP) comprising a polyvinyl alcohol carrier which exhibits a plurality of a scavenger structure which is capable of mitigating and/or neutralising the activity of a mediator of inflammatory-related conditions, said scavenger structure comprising carbazate as a nucleophilic centre, said AP being attached to a support made of a material selected from the group consisting plastic, glass, metal, mineral, ceramic and polymeric material.

2. The composition of claim 1, wherein,
the scavenger structure of the polyvinyl alcohol carrier further comprises b) a second nucleophilic centre which exhibits a single-bonded first heteroatom N, O or S (=$Y^1$) and complies with formula III $$Y^1(-R''-)(-R')_m H_n \qquad \text{(formula III)}$$

where:
a) $Y^1$ exhibits a free electron pair,
b) m is 0 or 1 and n is 1 or 2 with the sum of m plus n being 2 for $Y^1$=N and 1 for $Y^1$=S and O,
c) —R''— is a bivalent organic group providing attachment to the carrier via one of its free valences and direct attachment to the heteroatom $Y^1$ at the other one of its free valences, and
d) R'— is a monovalent organic group directly attached to the heteroatom $Y^1$ via its free valence; and
said first heteroatom $Y^1$ is capable of participating in an intramolecular addition reaction with a multiple bond formed when the carbazate is reacting with a keto or aldehyde carbon or a reactive multiple bond of an inflammatory related mediator.

3. The composition of claim 1, wherein the support is made of a polymeric material selected from the group consisting of polysaccharides and polyester polymers.

4. The composition of claim 1, wherein the AP is present in a concentration of 1 µg-100 mg/ml.

5. The composition of claim 1, wherein the polyvinyl alcohol carrier has 200-600 monomeric units.

6. A composition for treating or preventing inflammatory-related conditions, comprising as an active principle (=AP) a polyvinyl alcohol carrier which exhibits a plurality of a scavenger structure which is capable of mitigating and/or neutralising the activity of a mediator of inflammatory-related conditions, said scavenger structure comprising carbazate as a nucleophilic centre, said polyvinyl alcohol being attached to polysaccharide support.

7. The composition of claim 6, wherein the AP is present in a concentration of 1 µg-100 mg/ml.

8. The composition of claim 6, wherein the polyvinyl alcohol carrier has 200-600 monomeric units.

* * * * *